(12) United States Patent
Reiner et al.

(10) Patent No.: US 6,221,667 B1
(45) Date of Patent: Apr. 24, 2001

(54) METHOD AND COMPOSITION FOR MODULATING AMYLOIDOSIS

(75) Inventors: Peter B. Reiner; Bruce P. Connop, both of Vancouver (CA)

(73) Assignee: The University of British Columbia, Vancouver, British Columbia ( * ) Notice: Subject to any disclaimer, the term of this patent is extended or adjusted under 35 U.S.C. 154(b) by 0 days.

(21) Appl. No.: 09/383,317

(22) Filed: Aug. 25, 1999

Related U.S. Application Data

(63) Continuation of application No. 09/080,141, filed on May 15, 1998, now Pat. No. 5,981,168.

(51) Int. Cl.[7] .................. G01N 33/53; C12Q 1/00
(52) U.S. Cl. .................. 435/975; 435/4; 514/741
(58) Field of Search .................. 435/975, 4; 514/741

(56) References Cited

U.S. PATENT DOCUMENTS

| | | | |
|---|---|---|---|
| 3,637,845 | 1/1972 | Moore et al. | 564/80 |
| 5,049,574 | 9/1991 | Audiau et al. | 514/395 |
| 5,260,297 | 11/1993 | Jimonet et al. | 514/255 |
| 5,705,501 | 1/1998 | DeBernardis et al. | 514/255 |

FOREIGN PATENT DOCUMENTS

| | | |
|---|---|---|
| WO 92/00746 | 1/1992 | (WO) . |
| WO 92/02234 | 2/1992 | (WO) . |
| WO 92/14456 | 9/1992 | (WO) . |
| WO 95/21612 | 8/1995 | (WO) . |

OTHER PUBLICATIONS

Gabuzda et al., *J. Biol. Chem.*, 269(18):13623–13628 (1994).

Peterson et al., *Neuroscience Lett.*, 121:239–243 (1991).

Chemical abstract STN database accession number: 124:44716 HCA XP002114450 (1995).

*Primary Examiner*—Louise N. Leary
(74) *Attorney, Agent, or Firm*—Lahive & Cockfield, LLP; Nicholas P. Triano, III

(57) ABSTRACT

Methods and compositions, useful in the treatment of amyloidosis and conditions and diseases associated therewith, such as Alzheimer's Disease (AD). These methods involve administering to a subject a pharmaceutical composition including one or more agents which modulate APP catabolism and amyloid deposition. Accordingly, the methods and compositions are useful for inhibiting amyloidosis in disorders in which amyloid deposition occurs. The methods are based, at least in part, on modulating catabolism of APP in APP-containing cells through the use of a mobile ionophore, such as carbonyl cyanide p-(trifluoromethoxy) phenylhydrazone, which does not substantially alter the viability of those cells.

24 Claims, 7 Drawing Sheets

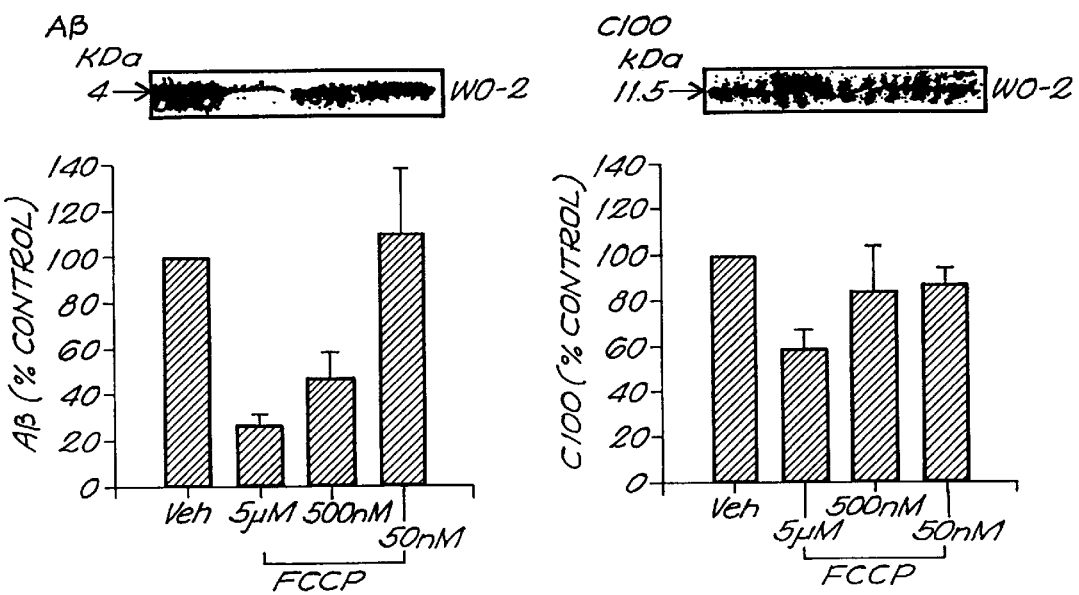
FIG. 2A  FIG. 2B
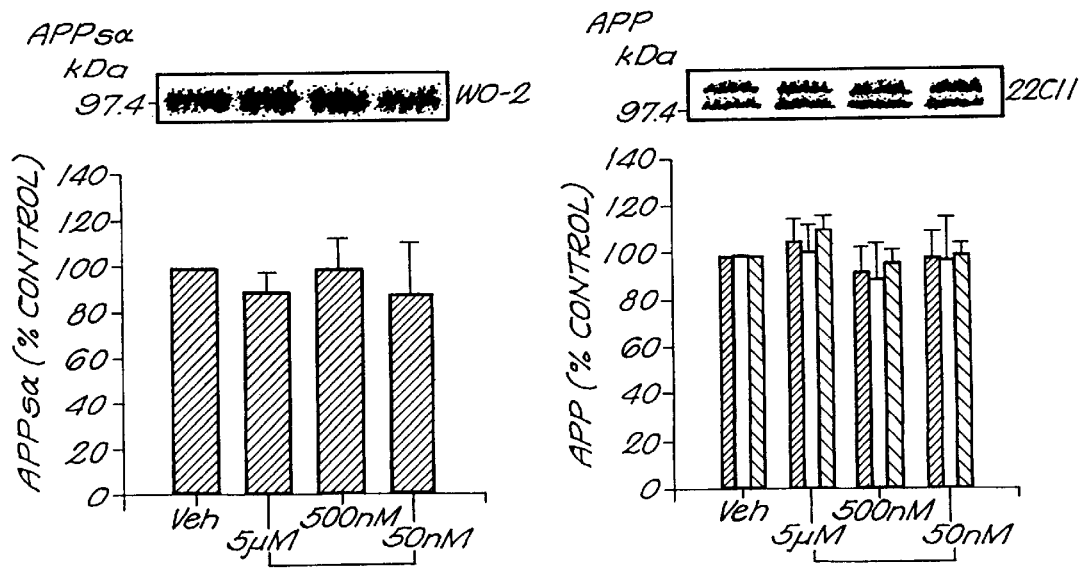
FIG. 2C  FIG. 2D

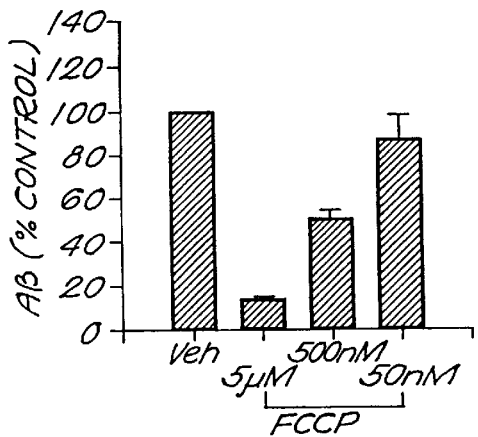
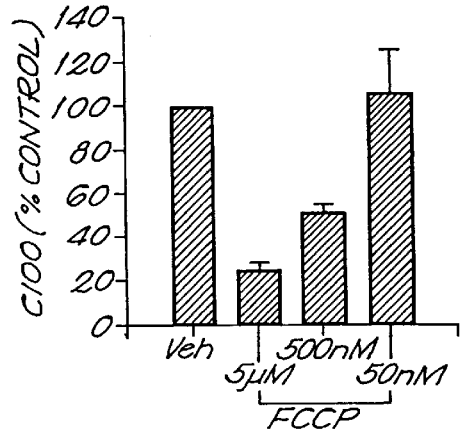
FIG. 3A  FIG. 3B
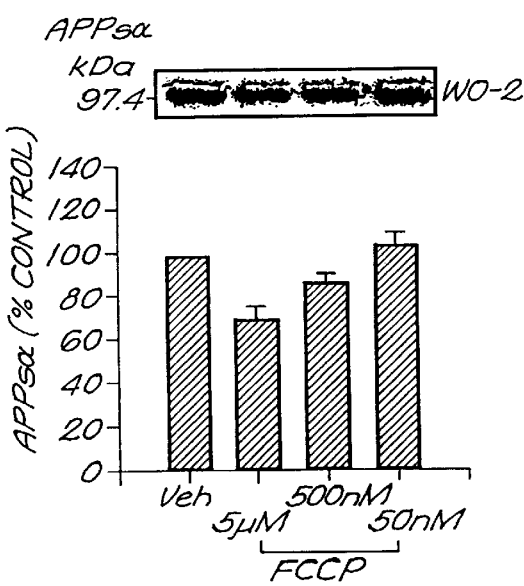
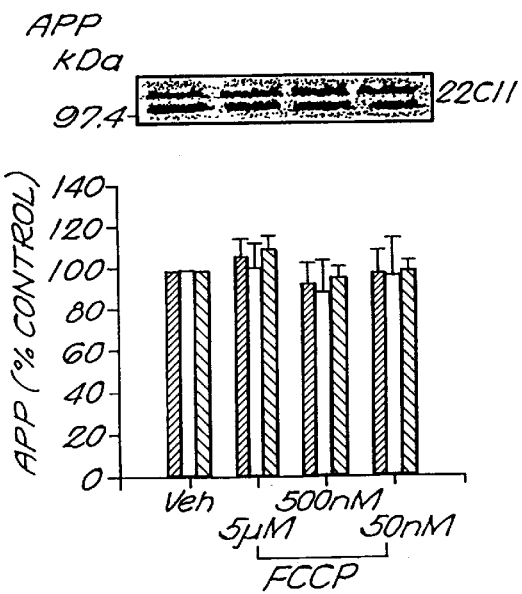
FIG. 3C  FIG. 3D

METHOD AND COMPOSITION FOR MODULATING AMYLOIDOSIS

This application is a continuation of application Ser. No. 09/080,141 filed on May 15, 1998, now U.S. Pat. No. 5,981,168.

BACKGROUND OF THE INVENTION

Alzheimer's disease (AD) is a common dementing brain disorder of the elderly. The key features of the disease include progressive memory impairment, loss of language and visuospatial skills, and behavior deficits. These changes in cognitive function are the result of degeneration of neurons in the cerebral cortex, hippocampus, basal forebrain, and other regions of the brain. Neuropathological analyses of postmortem Alzheimer's diseased brains consistently reveal the presence of large numbers of neurofibrillary tangles in degenerated neurons and neuritic plaques in the extracellular space and in the walls of the cerebral microvasculature. The neurofibrillary tangles are composed of bundles of paired helical filaments containing hyperphosphorylated tau protein (Lee, V. M and Trojanowski, J. Q, The disordered Cytoskeleton in Alzheimer's disease, *Curr. Opin. Neurobiol.* 2:653 (1992)). The neuritic plaques consist of deposits of proteinaceous material surrounding an amyloid core (Selkoe, D. J., "Normal and abnormal biology of the β-amyloid precursor protein", *Annu. Rev. Neurosci.* 17:489–517 (1994)).

Evidence suggests that deposition of amyloid-β peptide (Aβ) plays a significant role in the etiology of Alzheimer's disease. A portion of this evidence is based upon studies which have been generated from data with regard to familial Alzheimer's disease. To date, this aggressive form of Alzheimer's disease has been shown to be caused by missense mutations in (at least) three genes: the amyloid precursor protein (APP) gene itself (Goate, A. et al., "Segregation of a missense mutation in the amyloid precursor protein gene with familial Alzheimer's disease", *Nature* 349:704–706 (1991) and Mullan, M. et al., "A pathogenic mutation for probable Alzheimer's disease in the APP gene at the N-terminus of β-amyloid", *Nature Genet.* 1:345–347 (1992)), and two genes termed presenilins 1 and 2 (Sherrington, R. et al., "Cloning of a gene bearing missense mutations in early-onset familial Alzheimer's disease", *Nature* 375:754–760 (1995) and Rogaev, E. I. et al., "Familial Alzheimer's disease in kindreds with missense mutations in a gene on chromosome 1 related to the Alzheimer's disease type 3 gene", *Nature* 376:775–778 (1995)). The missense mutations in APP are located in the region of the protein where proteolytic cleavage normally occurs (see below), and expression of at least some of these mutants results in increased production of Aβ (Citron, M. et al., "Mutation of the β-amyloid precursor protein in familial Alzheimer's disease increases β-amyloid production", *Nature* 360:672–674 (1992), Cai, X-D. et al., "Release of excess amyloidβ protein from a mutant amyloidβ protein precursor", *Science* 259:514–516 (1993) and Reaume, A. G. et al., "Enhanced amyloidogenic processing of the beta-amyloid precursor protein in gene-targeted mice bearing the Swedish familial Alzheimer's disease mutations and a humanized Aβ sequence", *J. Biol. Chem.* 271:23380–23388 (1996)). Initial analyses of the structure of the presenilins have not suggested whether or not they might alter production of Aβ, however, recent data has indicated that these mutations cause an increase in Aβ secretion (Martins, R. N. et al., "High levels of amyloid-β protein from S182 (Glu$^{246}$) familial Alzheimer's cells", 7:217–220 (1995) and Scheuner, D. et al., "Secreted amyloid beta-protein similar to that in the senile plaques of Alzheimer's disease is increased in vivo by presenilin 1 and 2 and APP mutations linked to familial Alzheimer's disease", *Nature Medicine* 2:864–870 (1996)). Thus, increased production of Aβ is associated with Alzheimer's disease. Corroborating evidence has been derived from at least two other sources. The first is that transgenic mice which express altered APP genes exhibit neuritic plaques and age-dependent memory deficits (Games, D. et al., "Alzheimer-type neuropathology in transgenic mice overexpressing V717F β-amyloid precursor protein", *Nature* 373:523–525 (1995); Masliah, E. et al., "Comparison of neurodegenerative pathology in transgenic mice overexpressing V717F β-amyloid precursor protein and Alzheimer's disease", *J. Neurosci.* 16:5795–5811 (1996); Hsiao, K. et al., "Correlative memory deficits, Aβ elevation, and amyloid plaques in transgenic mice", *Science* 274:99–103 (1996)). The second piece of evidence comes from study of patients suffering from Down's syndrome, who develop amyloid plaques and other symptoms of Alzheimer's disease at an early age (Mann, D. M. A. and M. M. Esiri, "The pattern of acquisition of plaques and tangles in the brains of patients under 50 years of age with Down's syndrome", *J. Neuro Sci.* 89:169–179 (1989)). Because the APP gene is found on chromosome 21, it has been hypothesized that the increased gene dosage which results from the extra copy of this chromosome accounts for the early appearance of amyloid plaques (Kang, J. et al., "The precursor protein of Alzheimer's disease amyloid A4 protein resembles a cell-surface receptor", *Nature* 325:733–736 (1987); Tanzi, R. E. et al., "Amyloid β protein gene: cDNA, mRNA distribution and genetic linkage near the Alzheimer locus", *Science* 235:880–884 (1987)). Taken together with the evidence derived from cases of familial Alzheimer's disease, the current data suggests that genetic alterations which result in an increase in Aβ production can induce Alzheimer's disease. Accordingly, since Aβ deposition is an early and invariant event in Alzheimer's disease, it is believed that treatment which reduces production of Aβ will be useful in the treatment of this disease.

The principal component of the senile plaque is the 4 kDa β-amyloid peptide (Aβ). Ranging between 39 and 43 amino acids in length, Aβ is formed by endoproteolysis of APP. Alternative splicing generates several different isoforms of APP; in neurons, the predominant isoform is of 695 amino acids in length (APP695). As APP traverses the endoplasmic reticulum (ER) and trans-Golgi network (TGN), it becomes N- and O-glycosylated and tyrosine-sulfated. Mature holoprotein can be catabolized in several compartments to produce both non- and amyloidogenic APP fragments.

APP is expressed and constitutively catabolized in most cells. The dominant catabolic pathway appears to be cleavage of APP within the Aβ sequence by an enzyme provisionally termed α-secretase, leading to release of a soluble ectodomain fragment known as APPsα. In contrast to this non-amyloidogenic pathway, APP can also be cleaved by unidentified enzymes known as β- and γ-secretase at the N- and C-termini of the Aβ, respectively, followed by release of Aβ into the extracellular space. Several different C-terminal fragments are produced as intermediates in APP catabolic processing; of particular interest is the production of an intracellular an 12 kDa C-terminal fragment (C100) which is produced following β-secretase activity and contains the entire Aβ sequence.

Abundant evidence suggests that extracellular accumulation and deposition of A β is a central event in the etiology of AD. However, recent studies have also proposed that increased intracellular accumulation of Aβ or amyloid containing C-terminal fragments may play a role in the pathophysiology of AD. For example, overexpression of APP harboring mutations which cause familial AD results in the increased intracellular accumulation of C100 in neuronal cultures and A$\beta_{42}$ in HEK 293 cells. Moreover, evidence suggests that intra- and extracellular Aβ are formed in distinct cellular pools in hippocampal neurons and that a common feature associated with two types of familial AD mutations in APP ('Swedish' and 'London') is an increased intracellular accumulation of A$\beta_{42}$. Thus, based on these studies and earlier reports implicating extracellular Aβ accumulation in AD pathology, it appears that altered APP catabolism may be involved in disease progression.

Numerous studies have suggested that proteolytic cleavage of APP occurs within acidic compartments of the cell based on the inhibitory actions of agents which are known to disrupt intracellular pH and/or acidic organelles. For example, exposure of cells to the monovalent ionophore, monensin, or high concentrations of ammonium chloride ($NH_4Cl$) been shown to decrease APP proteolytic processing accompanied by concomitant alterations in full-length cellular APP. Similarly, the vacuolar $H^+$-ATPase inhibitor bafilomycin A1 (baf A1) has been reported to produce alterations in APP catabolism which are both cell-type and APP mutation specific. However, the ionophores noted above have been found to be toxic, unacceptably inhibit ATP formation, and alter cellular viability and endosomal and lysosomal function.

Thus, in view of the anticipated benefits of modulating APP catabolism as a treatment for diseases such as AD, compositions and methods for modulating APP catabolism in APP-containing cells which do not substantially alter the viability of those cells, have been desired and are addressed by the present invention.

SUMMARY OF THE INVENTION

This invention provides methods and compositions, which are useful in the treatment of amyloidosis and conditions and diseases associated therewith, such as Alzheimer's Disease (AD). The methods of the invention involve administering to a subject a pharmaceutical composition including one or more agents which modulate APP catabolism and ultimately, amyloid deposition. Accordingly, the methods and compositions of the invention are useful for inhibiting amyloidosis in disorders in which amyloid deposition occurs. The methods of the invention can be used therapeutically to treat amyloidosis or can be used prophylactically in a subject susceptible to amyloidosis. The methods of the invention are based, at least in part, on modulating catabolism of APP in APP-containing cells through the use of a mobile ionophore, such as carbonyl cyanide p-(trifluoromethoxy)phenylhydrazone, which does not substantially alter the viability of those cells. Therefore, the mobile ionophores disclosed herein can modulate amyloid deposition.

The present invention provides methods for modulating APP catabolism, by administering to APP-containing cells an amount of a mobile ionophore composition effective to modulate APP catabolism without substantially altering the viability of said APP-containing cells. In one preferred embodiment, the modulation includes preventing or inhibiting the amyloid deposition.

The present invention also provides methods for treating a disease state associated with amyloidosis by administering to a subject having APP-containing cells a pharmaceutically effective amount of a mobile ionophore composition effective to modulate APP catabolism without substantially altering the viability of the APP-containing cells. In one preferred embodiment, the disease state associated with amyloidosis is associated with Alzheimer's Disease.

The present invention further pertains to packaged pharmaceutical compositions for treating a disease state associated with amyloidosis. The package includes a container for holding an effective amount of a pharmaceutical composition and instructions for using the pharmaceutical composition for treatment of amyloidosis. The pharmaceutical composition includes a mobile ionophore composition effective to modulate APP catabolism in APP-containing cells. In one preferred embodiment, the packaged pharmaceutical composition is for treatment associated with Alzheimer's Disease.

The present invention further pertains to pharmaceutical compositions for treating amyloidosis, including a therapeutically effective amount of a mobile ionophore composition effective to modulate APP catabolism in APP-containing cells without substantially altering the viability of the APP-containing cells, and a pharmaceutically acceptable vehicle.

The present invention further pertains to methods for modulating amyloid deposition in a subject, including administering to a subject having APP-containing cells an effective amount of a mobile ionophore composition effective to modulate APP catabolism without substantially altering the viability of the APP-containing cells, such that modulation of amyloid deposition occurs.

BRIEF DESCRIPTION OF THE DRAWINGS

FIG. 2 illustrates FCCP reduction of Aβ release from mutant APP at 30 minutes in K695sw cells.

FIG. 3 illustrates FCCP reduction of Aβ release from mutant APP at 4 hours in K695sw cells.

DETAILED DESCRIPTION OF THE INVENTION

Figure 1A:
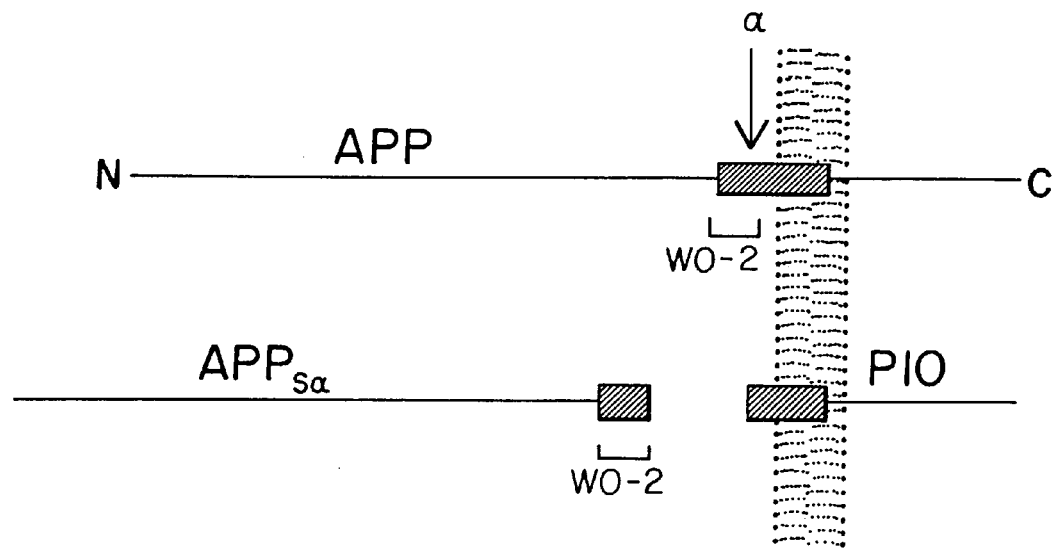
FIG. 1 generally illustrates APP catabolism.

The present invention pertains to methods for modulating APP catabolism via the use of mobile ionophore compositions to modulate APP catabolism in APP-containing cells without substantially altering the viability of those cells. Modulation of, e.g., reducing, APP catabolism, results in a decreased production of amyloid-β protein (Aβ) or increasing production of soluble amyloid precursor protein ($APP_s$), which are associated with amyloidosis and conditions related thereto, such as Alzheimer's disease.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In one embodiment, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls having one to three carbon atoms.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. A heteroalkyl moiety is an alkyl substituted with a heteroaromatic group.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, aralkyl, or an aromatic or heteroaromatic moiety.

The language "modulation of amyloid deposition" as used herein, means that amyloid deposition is prevented or decreased, e.g. A$\beta$ deposition. This modulation can be by one or more chemically induced physiological mechanisms. For example, the mobile ionophore compositions of the present invention can modulate amyloidosis in a subject such as by modulating APP catabolism, thereby decreasing production of amyloid-$\beta$ protein (A$\beta$) or increasing production of soluble amyloid precursor protein (APP$_s$).

The language "modulation of APP catabolism" as used herein, means that APP catabolism is prevented or decreased. This modulation can be by one or more chemically induced physiological mechanisms. For example, the dominant catabolic pathway appears to be cleavage of APP within the A$\beta$ sequence by an enzyme provisionally termed $\alpha$-secretase, leading to release of a soluble ectodomain fragment known as APPs$\alpha$. In contrast to this non-amyloidogenic pathway, APP can also be cleaved by unidentified enzymes known as $\beta$- and $\gamma$-secretase at the N- and C-termini of the A$\beta$, respectively, followed by release of A$\beta$ into the extracellular space. Several different C-terminal fragments are produced as intermediates in APP catabolic processing; such as the production of an intracellular an 12 kDa C-terminal fragment (C100) which is produced following β-secretase activity and contains the entire Aβ sequence.

The term "subject" is intended to include mammals having amyloid deposition, including one or more amyloid-related symptoms, or which are susceptible to amyloid deposition. Examples of such subjects include humans, dogs, cats, pigs, cows, horses, rats and mice.

The term "mobile ionophore composition" is intended to refer to compositions which disrupt intracellular pH, as is believed to be important in the present disclosure, e.g., uncouplers of oxidative phosphorylation. The mobile ionophore compositions of the present invention have the effect of modulating APP catabolism in APP-containing cells without substantially altering the viability of those cells. In an advantageous embodiment, the mobile ionophore compositions are of the formula

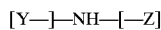 (I)

wherein Y is a hydrophobic/lipophilic moiety; N is nitrogen; and Z is H or an electron-withdrawing moiety; provided that when Z is H, Y further comprises an electron-withdrawing moiety thereon.

"Hydrophobic/lipophilic moiety" is intended to refer to moieties which are hydrophobic and/or lipophilic in nature. Advantageously, such moieties allow the mobile ionophore to position itself within the lipid bilayer of a cell membrane such that the mobile ionophore composition functions as, e.g., a protonophore, so as to conduct protons across the membrane.

Examples of hydrophobic/lipophilic moieties include aryl, aralkyl, aryl heterocycles, polycycyls, and heterocyclyls, such as benzene, pyrrole, furan, thiophene, imidazole, oxazole, thiazole, triazole, pyrazole, pyridine, pyrazine, pyridazine and pyrimidine, naphthyl, quinolyl, indolyl, tetralin, pyrrolidine, oxolane, thiolane, oxazole, piperidine, piperazine, morpholine, lactones, lactams, pyrrolidinones, lactones, sultams, and sultones. A preferred hydrophobic/lipophilic moiety is benzyl.

"Electron-withdrawing moiety" is intended to refer to moieties which are electron-withdrawing in nature, such as chemical groups associated with a relatively high electronegativity, like halogen atoms (e.g., fluorine or chlorine), or mono-, di-, or tri-halosubstituted, alkyl, alkylsulfonyl, or alkoxy groups. Examples of these groups include carbonyl cyano, trifluoromethanesulfonyl, trifluoromethoxy, and trifluoroethoxy. The presence of such electron-withdrawing moieties on preferred mobile ionophores disclosed herein is believed to enhance their properties as protonophores. In particular, the electron-withdrawing moiety(s) are believed to promote the protonization/deprotonization capability of the nitrogen atom in formula (I), which is believed to be important to the actions of the molecule in vivo. The presence of more than one electron-withdrawing moiety on the molecule is believed to be particularly advantageous; for example, in the above formula (I), in embodiments where Z is an electron-withdrawing moiety, the Y hydrophobic/lipophilic moiety may be substituted with one or more electron-withdrawing moieties, e.g., a p-substituted aryl group. Particularly preferred electron-withdrawing groups are trifluoromethanesulfonyl, trifluoromethoxy, trifluoroethoxy, and carbonyl cyano groups.

In another embodiment the mobile ionophore composition is of the formula:

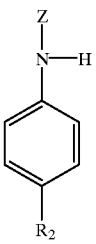 (II)

wherein $R_2$ is H, an alkyl group, an alkoxy group, or an electron-withdrawing moiety; Z is H, an alkyl group, an alkoxy group, or an electron-withdrawing moiety. In a preferred embodiment Z and $R_2$ are electron-withdrawing moieties.

Desirably, Z and $R_2$ are electron-withdrawing moieties, which may be, e.g., trifluoromethanesulfonyl, trifluoromethoxy, trifluoroethoxy, or carbonyl cyano groups. Desirably, $R_2$ is an alkoxy group which contains one or more halogen atoms thereon, such as a mono-, di-, or tri-halomethoxy group. In another embodiment $R_2$ is a trifluoromethoxy group and Z is —NC(CN)$_2$. In yet another embodiment, Z is —SO$_2$R$_4$ where $R_4$ is a mono-, di- or tri-halomethyl group.

Preferred mobile ionophore compositions include carbonyl cyanide p-(trifluoromethoxy)phenylhydrazone, carbonyl cyanide m-chlorophenylhydrazone, N[4-(tetrafluoroethoxy)phenyl]-1,1,1-trifluoromethanesulfonamide, N-[4-chlorophenyl]-1,1,1-trifluoromethanesulfonamide, N-[4-(tetrafluoromethoxy)phenyl]-1,1,1-trifluoromethanesulfonamide, N-[4-(methylthio)phenyl]-1,1,1-trifluoromethanesulfonamide, N-[4-(t-butyl)phenyl]-1,1,1-trifluoromethanesulfonamide, N-[4-fluorophenyl]-1,1,1-trifluoromethanesulfonamide, N-phenyl-1,1,1-trifluoromethanesulfonamide, N-[4-(ethoxy)phenyl]-1,1,1-trifluoromethanesulfonamide, N-[4-(N, N-dimethylamino)phenyl]-1,1,1-trifluoromethanesulfonamide, N-[4-cyanophenyl]-1,1,1-trifluoromethanesulfonamide, and N-[4-(methylsulfonyl)phenyl]-1,1,1-trifluoromethanesulfonamide.

The term "administering" is intended to include routes of administration which allow the mobile ionophore composition to perform its intended function, e.g., preventing or inhibiting amyloidosis. A variety of routes of administration are possible including, but not necessarily limited to parenteral (e.g., intravenous, intraarterial, intramuscular, subcutaneous injection), oral (e.g., dietary), topical, nasal, rectal, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. (1980)).

The language "effective amount" is that amount of the mobile ionophore composition which allows it to perform its intended function. For example, an effective amount is that amount sufficient to inhibit, partially or totally, APP catabolism and thus prevent or reduce further amyloid deposition. The "effective amount" also includes the amount sufficient to treat amyloidosis or Alzheimer's disease. The effective amount will depend upon a number of factors, including biological activity of the mobile ionophore composition, age, body weight, sex, general health, severity of the disease to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

The term "amyloidosis" is art recognized and is intended to include amyloid deposition related symptoms, such as progressive and undesirable memory impairment, loss of language and visuospatial skills, and behavior deficits. These changes in cognitive function are the result of degeneration of neurons in the cerebral cortex, hippocampus, basal forebrain, and other regions of the brain. The presence of large numbers of neurofibrillary tangles in degenerated neurons, neuritic plaques in the extracellular space and in the walls of the cerebral microvasculature are a result of amyloid deposition. For example, neuritic plaques which consist of deposits of proteinaceous material surrounding an amyloid core.

The present invention further pertains to packaged pharmaceutical compositions for treating amyloidosis. The package includes a container for holding an effective amount of a pharmaceutical composition and instructions for using the pharmaceutical composition for treatment of amyloidosis. The pharmaceutical composition includes at least one mobile ionophore composition for modulating APP catabolism in a subject.

The term "pharmaceutical composition" includes mobile ionophore compositions of the present invention and includes ingredients, such as other therapeutically active substances, inert ingredients, and carrier compounds. The components of the composition must be compatible, meaning that the components must be capable of being commingled with the active substance, e.g., the mobile ionophore composition, and with each other in a manner such that there is no interaction which would substantially reduce during use the composition's efficacy for modulating amyloid deposition.

The pharmaceutical compositions can be prepared by known procedures using well known and readily available ingredients. In making the pharmaceutical compositions of the present invention, the active substance will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing up to 10% by weight of the active compound, soft and hard gelatin capsules, packaged powders, and the like. Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, propylhydroxybenzoates, talc, and other compounds as are well known to those skilled in the pharmaceutical arts.

The term "organism" is intended to include single cells, such as *C. elegans*, multicell organisms, such as yeast, and cell lines. Multicell organisms include small mammals, such as mice, rats, guinea pigs, and pigs that can develop amyloidosis.

The term "model system" includes cells, cell lines and mammals, such as mice, rats and pigs.

The invention is further illustrated by the following exemplification which in no way should be construed as being further limiting. The contents of all references, pending patent applications and published patent applications, cited throughout this application are hereby incorporated by reference. It should be understood that the animal cell line model(s) used throughout the examples are accepted cell models and that the demonstration of efficacy in these cell models is predictive of efficacy in humans.

EXEMPLIFICATION

Cell Lines and Drug Treatments

Human embryonic kidney (HEK) 293 cells stably transfected with either wild-type $APP_{695}$ (K695 cells) or APP carrying the AD-linked double "Swedish" mutation (K695sw cells)(30) were cultured in DMEM supplemented with sodium pyruvate (1 mM) and 10% fetal calf serum as previously described (31). Cells were plated at 1,000,000 cells per well in 35 $mm^2$ culture dishes (Corning™) 24 hours prior to drug exposure. Preceding the addition of drugs, cultures are washed once with warm PBS (37° C.) and then exposed to various treatments in DMEM supplemented with sodium pyruvate (1 mM). Cultures were then exposed to either control media, vehicle (0.05% ethanol), or varying concentrations of FCCP (5 $\mu$M, 500 nM, 50 nM). Either 30 minutes or 4 hours after the addition of drugs, the media was removed, the cultures washed once with ice-cold PBS, and then harvested in 100 $\mu$l of ice-cold lysis buffer containing 20 mM MOPS (pH 7.2), 5 mM EDTA, 0.01% NP-40, 75 mM β-glycerol phosphate, 200 mM DTT, 100 mM sodium vanadate, 50 mM phosphatase substrate, 100 mM PMSF, and 1 mg/ml each of leupeptin, aprotinin and pepstatin.

Detection of Intra- and Extracellular APP Catabolic Fragments

Figure 1B:
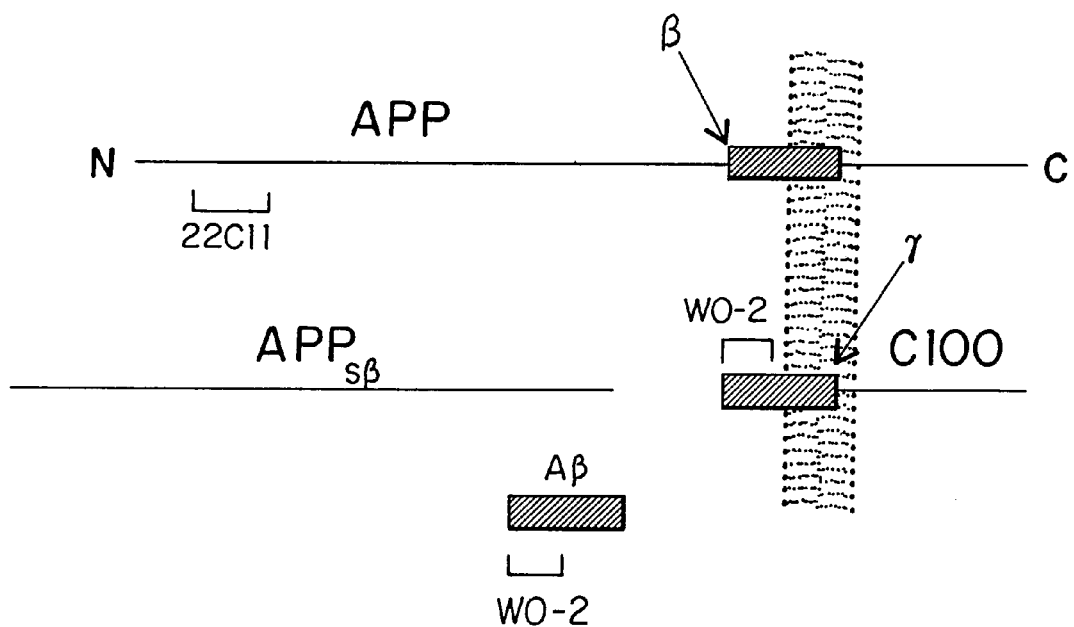

To examine extracellular APP fragments, the media was retained and centrifuged at 4° C. for 10 min at 16,000×g to remove cellular debris. Extracellular protein was then precipitated by 10% trichloroacetic acid as previously described (31). Subsequently, secreted APPsα was determined by 10% Tris-Glycine SDS-PAGE Western Blot analysis using the monoclonal antibody WO-2, generated against the first 16 amino acids of the N-terminal region of Aβ (32). Similarly, extracellular Aβ release was examined by 16% Tris-Tricine SDS-PAGE Western Blot analysis using the WO-2 antibody (32). For examination of intracellular APP fragments, cultures were harvested in ice-cold lysis buffer and then sonicated for 8 seconds on ice. Cellular protein levels were quantified using the BCA protein assay (Pierce, Rockford, Ill.) and 10 μg of cellular protein were then separated by either 10% Tris-Glycine or 16% Tris-Tricine SDS-PAGE. Intracellular C100 and total APP were quantitated, respectively, by 16% Tris-Tricine Western Blot analysis using the WO-2 antibody and 10% Tris-Glycine Western Blot analysis using an anti-APP N-terminal antibody (22C11, Boehringer Mannheim, Laval, QC). A diagram of the catabolic fragments of APP and the epitopes to which each antibody binds is depicted in FIG. 1. As seen in FIG. 1, the N-terminus of APP is extracellular, the C-terminus is intracellular. The wavy line represents the plasma membrane. The enzyme α-secretase (α-left) cleaves APP within the Aβ sequence (represented by the heavy line), resulting in release of the ectodomain fragment known as APPsα. The enzymes β and γ secretase (β, γ, right) sequentially cleave APP on either side of the Aβ sequence. β secretase cleavage results in the release of the ectodomain fragment known as APPsβ and production of the cellular fragment known as C100; following γ-secretase cleavage, extracellular Aβ is released. Probing the cellular fraction with antibody 22C11 identifies total cellular APP. Probing the cellular fraction with WO-2 identifies C100 (distinguished by molecular weight). Probing the extracellular fraction with WO-2 identifies both APPsα and Aβ (distinguished by molecular weight).

Cellular (C100 and total APP) and extracellular (APPsα and Aβ) APP catabolic fragments were separated using SDS PAGE with either 10% Tris-Glycine (for APPsα and total APP) or 16% Tris-Tricine (for C100 and Aβ) gels. Following electrophoretic separation, proteins were transferred to nitrocellulose membranes and probed with either the monoclonal antibody WO-2 to detect C 100, APPsα and Aβ, or 22C11 to detect total cellular APP. Immunoreactive bands were visualized using ECL detection (Amersham, Oakville, ON) and analyzed by standard autoradiographic and densitometric techniques as described (31).

Quantification of Cellular ATP Levels

K659sw cells were maintained, exposed to drugs, and harvested as described above with the exception that cells were plated at 500,000 cells per plate and the lysis buffer used consisted of 25 mM Tricine (pH 7.8), 270 mM sucrose and 1 mM EDTA. After harvesting, samples were centrifuged at 4° C. for 10 min at 16,000×g to remove cellular debris. 20 μl aliqouts of ATP standards and samples were then assayed for ATP content using a luciferase/luciferin ATP determination kit (A-6608, Molecular Probes, Eugene, Oreg.). ATP-dependent luminescence was quantified using an Optocomp® II luminometer (MGM Instruments, Hamden, Conn.) and ATP levels were determined by extrapolation from a standard curve. Cellular protein levels were quantified using the BCA protein assay (Pierce, Rockford, Ill.) and cellular ATP levels were expressed as μ mol/μg protein. As a positive control, the effect of combined treatment with various concentrations of sodium azide and 2-deoxy-D-glucose (NaA/DG) was also examined in these studies.

Assessment of Cell Viability

Cell viability was quantified based on the exclusion of the membrane impermeant probe, YO-PRO (Molecular Probes, Eugene, Oreg.). K695sw cells were maintained and exposed to vehicle or various concentrations of FCCP as described above with the exception that cells were plated at a density of 20,000 cells/well in 96-well plates (Falcon®). Twenty-four hours after plating, cells were exposed to various treatments in DMEM supplemented with sodium pyruvate (1 mM) and 10% fetal bovine serum. At the same time as drug exposures, YO-PRO (4 μM) was added to each well and its uptake quantified every 30 minutes for 1 day at 37° C. using a Cytofluor™ 2350 fluorometric plate reader (Millipore, Mississauga, ON). As a positive control, all wells were exposed to 0.1% Triton X-100 at the end of the experiment.

Quantitation and Visualization of Endosomal and Lysosomal Function

Endosomal function was assessed by the fluorometric quantitation of the receptor-mediated uptake of both Texas Red and fluorescein labelled transferrin (Molecular Probes, Eugene, Oreg.)(33–35). K695 cells were maintained as exposed to various treatments as mentioned with the exception that cells were plated at a density 200,000 cells/well in 24-well plates (Corning™). Twenty-four hours after plating, cells were exposed to various treatments in DMEM supplemented with sodium pyruvate (1 mM) and 10% fetal bovine serum. At the same time as drug exposures, both transferrin-Texas Red (Tf-Tx) and transferrin-fluoroscein (Tf-F) (10 μl/ml media of 5 mg/ml stocks in PBS) were added to each well and incubated for 4 hours at 37° C. Each well was then gently washed three times with warm media and uptake of fluorescent probes quantitated at 37° C. using a Cytofluor™ 2350 fluorometric plate reader (Millipore, Mississauga, ON). Quantitation of the non-pH-dependent Tf-Tx fluorescence and the pH-dependent Tf-F fluorescence was determined using excitation filters of 590 nm (bandwidth=20 nm); 485 nm (bandwidth=20 mn) and emission filters of 645 nm (bandwidth=40 nm); 530 nm (bandwidth=25 nm), respectively. Similarly, Lysosomal function was assayed by the uptake of the fluorescent probe, Lysosensor™ Yellow/Blue DND-160 (Molecular Probes, Eugene, Oreg.)(36). Assay of Lysosensor™ uptake was performed in an identical manner to that of the fluorescent labelled transferrin conjugates with the exception that the addition of 10 μl/ml media of Lysosensor™ was taken from a 1 mM stock solution in DMSO. Quantitation of the non-pH-dependent blue fluorescence and the pH-dependent yellow fluorescence was determined using an excitation filter of 360 nm (bandwidth=40 nm) and emission filters of 460 nm (bandwidth=40 nm) and 530 nm (bandwidth=25 nm), respectively. For all three probes examined, relative fluorescence was obtained from subtraction from sister wells which had not been exposed to fluorophores. Exposure of wells minus cells to probes and subsequent washing produced a similar signal as that observed from cellular autofluorescence. As positive controls in both transferrin and Lysosensor™ uptake experiments, sister wells were exposed to the agents, baf A1 (1 μM) and $NH_4Cl$ (20 mM), which are known to affect acidic cellular compartments.

For the direct visualization of the cellular distribution of the Tf-Tx, Tf-F and Lysosensor™ probes, K695 cells were grown, treated and exposed to fluorophores as above with the exception that cells were plated in 35 mm plates (Corning™) at a density of 750,000 cells/dish. Cultures were visualized and photographed through a water immersion lense (63×magnification) using an Axiophot® fluorescent Microscope (Zeiss, Germany) with the same excitation and emission filters as mentioned above.

Statistical Analysis

Statistical significance was determined using an ANOVA with Tukey's post hoc analysis. Data are expressed as mean±SEM with * p<0.05. Sequential Western Blots are representative of between 3 and 5 separate samples which may or may not have been taken from the same trial. n=4–8 for each treatment group in experiments quantitating cellular ATP levels, cell viability and endosomal/lysosomal function.

RESULTS

FCCP Inhibits APP Catabolism but not Maturation

We began our study using HEK 293 cells stably transfected with APP bearing the 'Swedish' mutation (K695sw cells), as detection of APP fragments is relatively straightforward in this cell line (30). Exposure of K695sw cells to the protonophore FCCP for 30 min resulted in a concentration-dependent decrease in A$\beta$ release. FIG. 2 illlustrates the effect of FCCP exposure to K695 cells at various concentrations for 30 minutes and cellular and released APP catabolic fragments quantified by Western blot analysis. The effect of FCCP on A) A$\beta$ release, B) cellular C100, C) APPs$\alpha$ release and D), total cellular APP are illustrated. In D) solid, white and hatched bars represent total, mature and immature APP, respectively. Data represent mean±SEM with * p<0.05.

Following 4 hours of FCCP treatment, decreases in A$\beta$ release were even more pronounced, and in addition there was a concentration-dependent decrease in the formation of the C100 fragment (FIGS. 3A, B). Production of the ectodomain fragment APPs$\alpha$ was only affected by 4 hour exposure to 5 $\mu$M FCCP, the highest concentration employed (FIG. 3C), while neither total cellular levels of APP nor the maturation of APP via N'/O' linked glycosylation were affected by FCCP (FIG. 3D). FIG. 3 illlustrates the effect of FCCP exposure at various concentrations for 4 hours and cellular and released APP catabolic fragments quantified by Western blot analysis. The effect of FCCP on A) A$\beta$ release, B) cellular C100, C) APPs$\alpha$ release and D), total cellular APP are illustrated. In D) solid, white and hatched bars represent total, mature and immature APP, respectively. Data represent mean±SEM with * p<0.05.

Figure 4A:
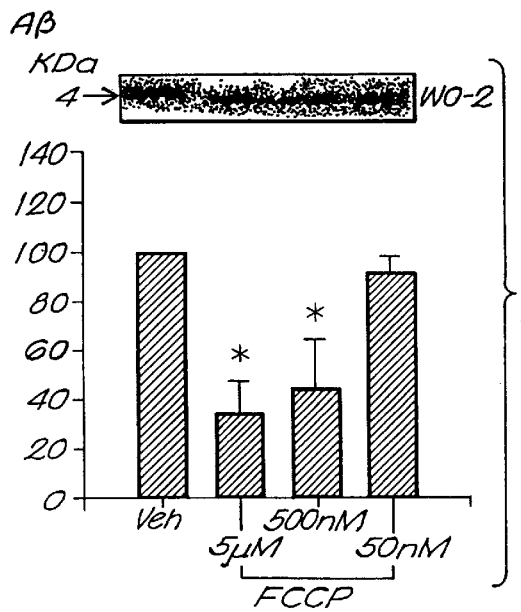
FIG. 4 illustrates FCCP inhibition of wild-type APP in K695 cells.
Figure 4B:
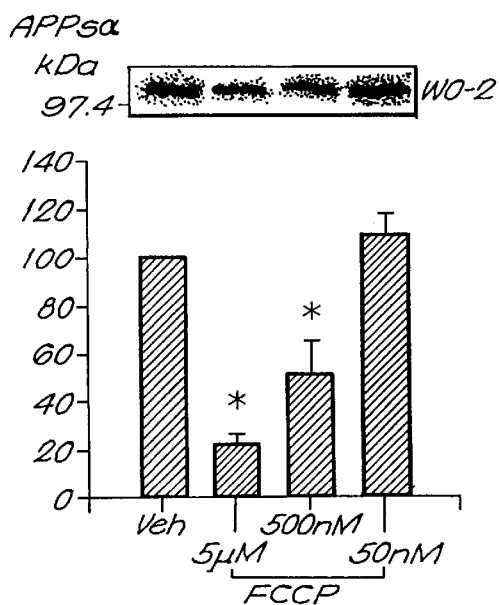
Figure 4C:
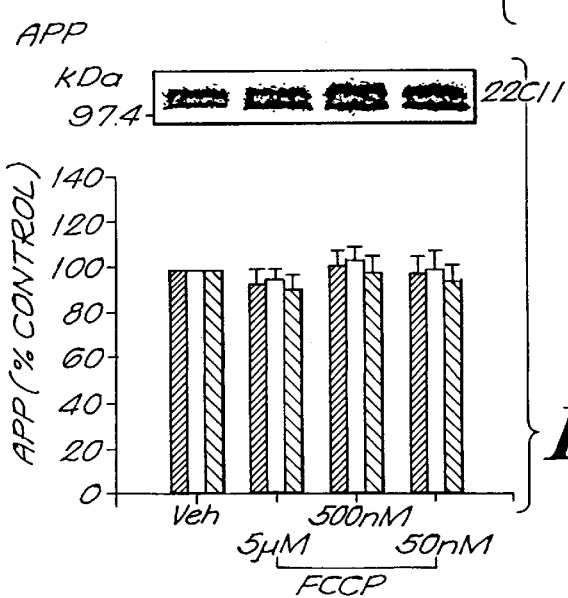

In previous studies it was shown that the proton-ATPase inhibitor, baf A1, reduced A$\beta$ production in K695sw cells but not in cells expressing wild-type APP. As both baf A1 and FCCP may act on acidic compartments, albeit via different mechanisms, we tested the effects of FCCP upon APP catabolism in HEK 293 cells stably transfected with wild-type APP$_{695}$ (K695 cells) (FIG. 4). In contrast to the lack of effect of baf A1 upon A$\beta$ production in K695 cells, treatment with FCCP for 4 hours clearly inhibited A$\beta$ production in a concentration-dependent manner. Moreover, in contrast to the modest effects of FCCP upon APPs$\alpha$ release from K695sw cells, treatment of K695 cells with FCCP for 4 hours also resulted in a marked concentration-dependent decrease in APPs$\alpha$ production. The effect of FCCP upon A$\beta$ and APPs$\alpha$ production did not appear to be secondary to effects upon protein maturation, as the both total levels of cellular APP as well as maturation of APP were unaffected (FIG. 4C). Because of the low levels of C100 found in K695 cells, we were unable to quantify the effects of FCCP upon this APP catabolic fragment. FIG. 4 illlustrates the effect of FCCP exposure at various concentrations for 4 hours and cellular and released APP catabolic fragments quantified by Western blot analysis. The effect of FCCP on A) A$\beta$ release, B) cellular C100, and C) total cellular APP are illustrated. In C) solid, white and hatched bars represent total, mature and immature APP, respectively. Data represent mean±SEM with * p<0.05.

FCCP does not Inhibit A TP Formation and is not Toxic

Figure 5A:
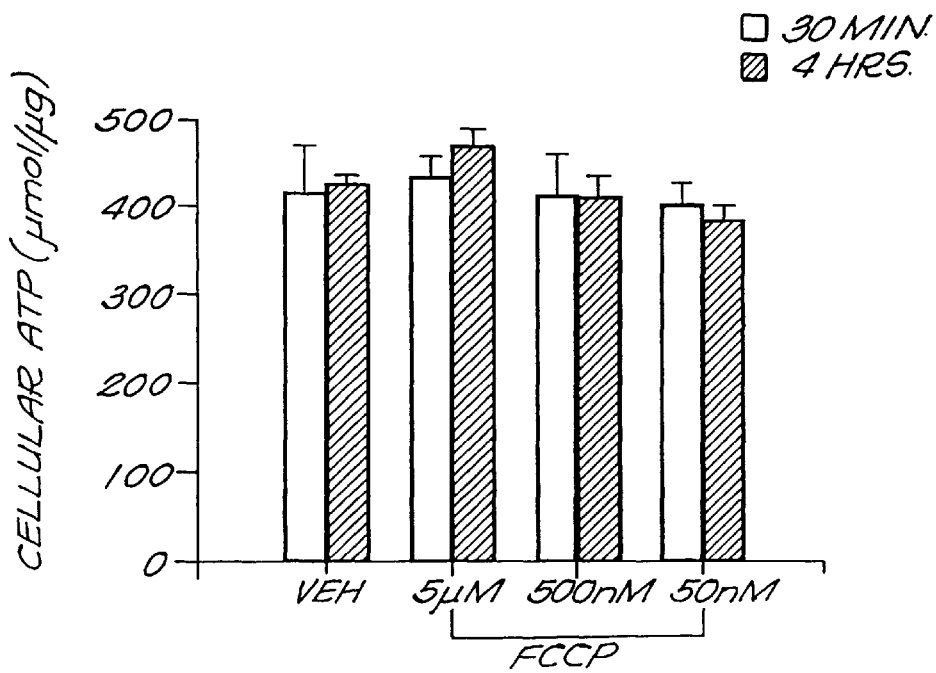
FIG. 5 illustrates FCCP effect on cellular ATP levels.
Figure 5B:
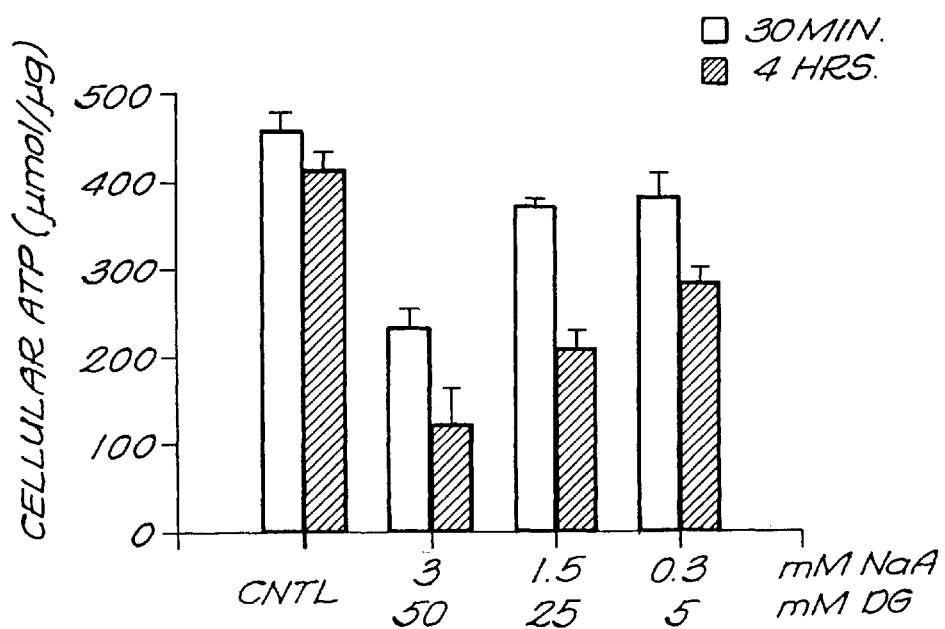

Since mitochondria utilize the proton gradient as a driving force for ATP generation, it has long been thought that FCCP and the class of mobile ionophores of which it is a member uncouple oxidative phosphorylation (37, 38). Indeed, it has been shown that 1 $\mu$M FCCP is sufficient to alter mitochondrial membrane potential (39) and that application of 30 $\mu$M FCCP for 2 hours is sufficient to modestly decrease cellular ATP levels (40). To determine whether the concentrations of FCCP which altered APP catabolism were sufficient to change ATP levels in K695sw cells, we measured ATP levels following exposure of these cells to various concentrations of FCCP (FIG. 5A). As a positive control, the effects of a combination treatment with NaA/DG on cellular ATP levels was also evaluated (FIG. 5B). As expected, treatment of K695sw cells with NaA/DG resulted in concentration- and time-dependent decreases in cellular ATP levels. However, treatment of cells with FCCP did not alter cellular ATP levels at any of the concentrations or time points measured. FIG. 5 illlustrates the effect of FCCP exposure at various concentrations for either 30 minutes (shaded) or 4 hours (solid) and cellular ATP levels quantitated by lucifern/luciferase bioluminescence assay (A). As a positive control, the ability of NaA/DG to deplete cellular ATP levels can be seen in (B). Data represent mean±SEM with * p<0.05.

Figure 6:
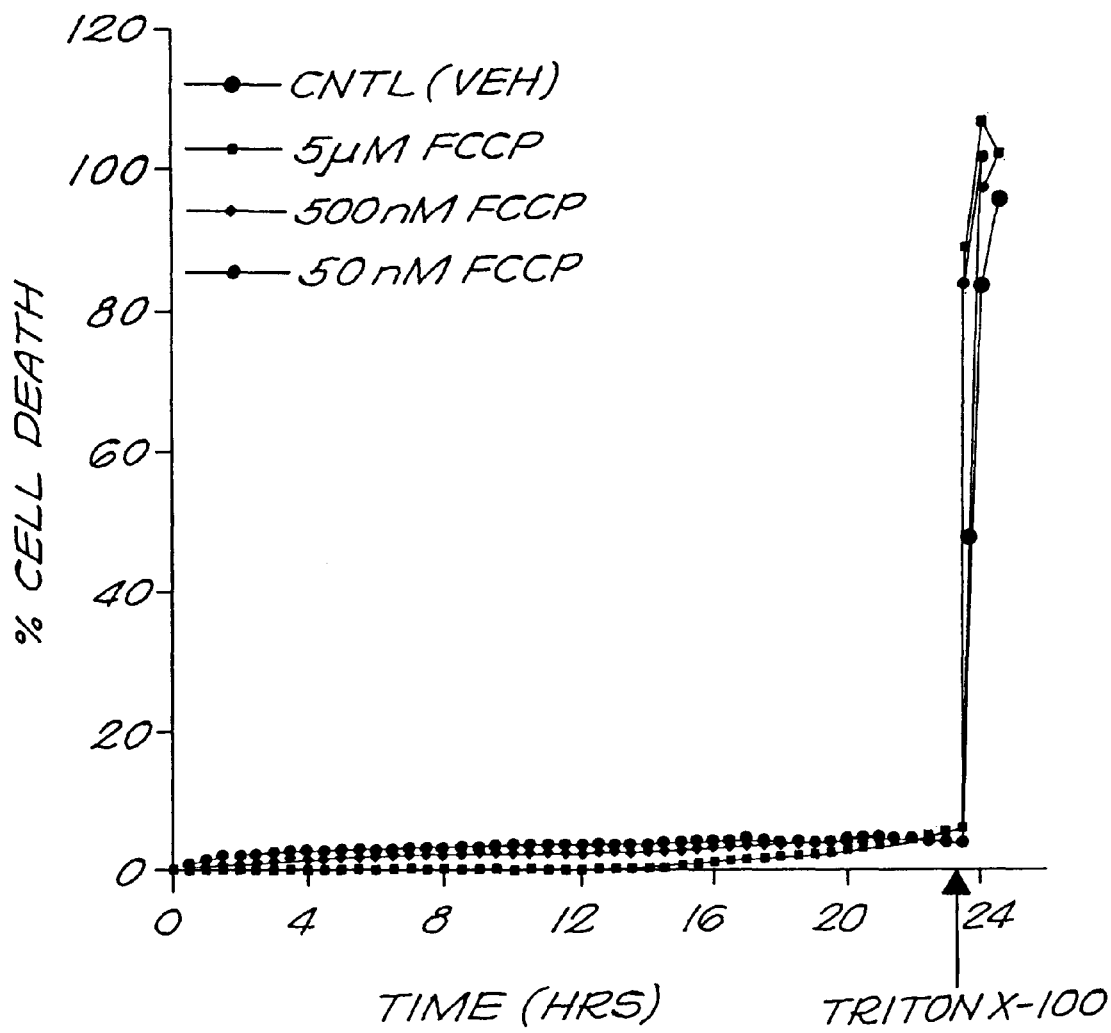
FIG. 6 illustrates the lack of toxicity of FCCP on K695sw cells.

As a further measure to ensure that the effects of FCCP were not due to altering the integrity of K695sw cells, we employed YO-PRO exclusion staining as a measure of cell viability. As can be seen in FIG. 6, even following 24 hours of exposure to FCCP, there was no increase in cell death as measured by membrane exclusion. Taken together, these data suggest that the effects of FCCP upon APP catabolism are independent of effects upon oxidative phosphorylation, and that concentrations of FCCP which markedly alter APP catabolism are not overtly toxic. FIG. 6 illustrates K695 exposure to vehicle (circles), 5 $\mu$M (squares), 500 nM (diamonds) or 50 nM (hexagons) FCCP for 24 hrs and cell viability assessed by the YO-PRO exclusion method. At the end of the experiment, 0.1% Triton X-100 was added to each well as a positive control. Data represent mean±SEM with * p<0.05.

Figure 7A:
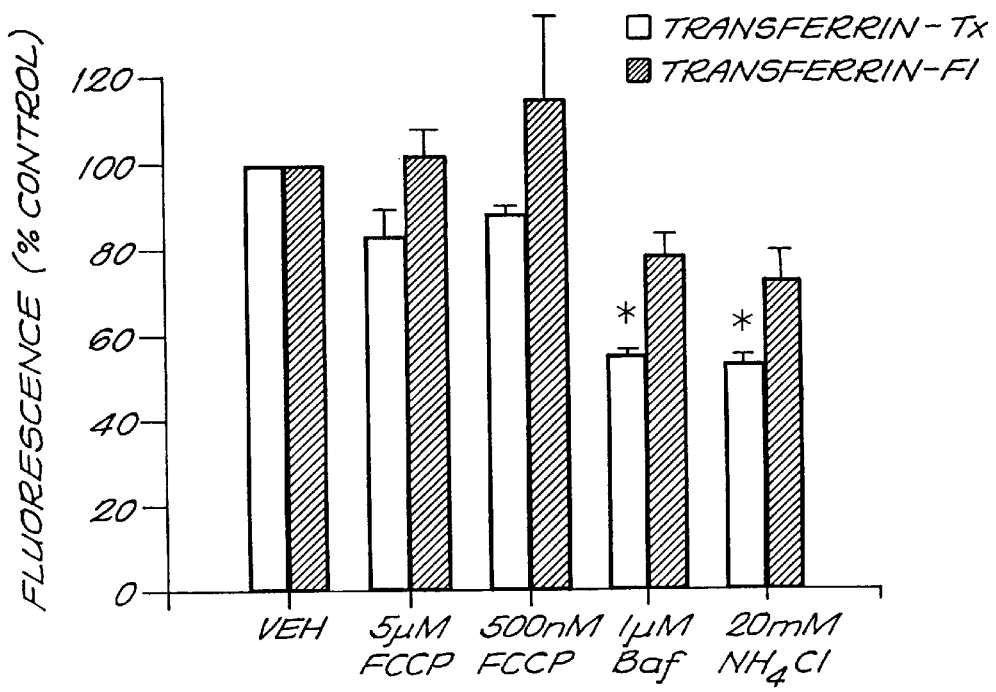
FIG. 7 shows a comparison of the effects of FCCP to baf A1 and $NH_4Cl$ on the endosomal/lysosomal function of K695sw cells.

FCCP does not Alter Endosomal Function and Effects Lysosomal Function Less than Bafilomycin A1 and NH$_4$Cl Based on the lack of effect of FCCP on cellular ATP levels we sought to ascertain the specific acidic compartment(s) through which deacidification by FCCP could account for a decrease in APP catabolism. Endosomal function was assessed by the receptor-mediated uptake of both Tf-Tx and Tf-F, which are non- and pH-sensitive endosomal probes, respectively. The use of these probes to measure endosomal function has been well characterized (33–35) and the pH-dependency of the Tf-F signal is based on the known sensitivity of fluoroscein to low pH whereby its fluorescent signal is diminished. Thus, decreases in Tf-Tx uptake represent decreased receptor-mediated internalization of transferrin and/or total endosomal number whereas increases in Tf-F fluorescence may be indicative of endosomal deacidification. However, a confounding complication with the use of Tf-F to quantitate endosomal pH is the fact that decreased tranferrin uptake or endosomal number will inherently decrease the Tf-F signal which makes relative increases in fluorescence due to endosomal deacidification more difficult to quantitate. Despite this, it was observed that in contrast to treatment with both baf A1 and NH$_4$Cl, FCCP did not significantly alter endosomal functioning (FIG. 7A). The decreases in both Tf-Tx and Tf-F signals observed following treatment with baf A1 and NH$_4$Cl indicate that these agents are able to impair endosomal function by approximately 50% at the concentrations employed. FIG. 7 illustrates illustrates K695 exposure to vehicle, FCCP (5 μM and 500 nM), baf A1 (1 μM) and NH$_4$Cl (20 mM) for 4 hrs and endosomal and lysosomal functioning assessed. Endosomal function was evaluated by the fluorescent quantitation of both the non-pH-dependent probe, Tf-Tx (shaded), and the pH-sensititive conjugate, Tf-F (solid) (A). Similarly, lysosomal function was measured by the fluorescent quantitation of both the blue (shaded) and yellow (solid) emission spectras of Lysoscnsor™ which are more predominant in less and more acidic lysosomes, respectively (B). Data represent mean±SEM with * p<0.05.

Figure 7B:
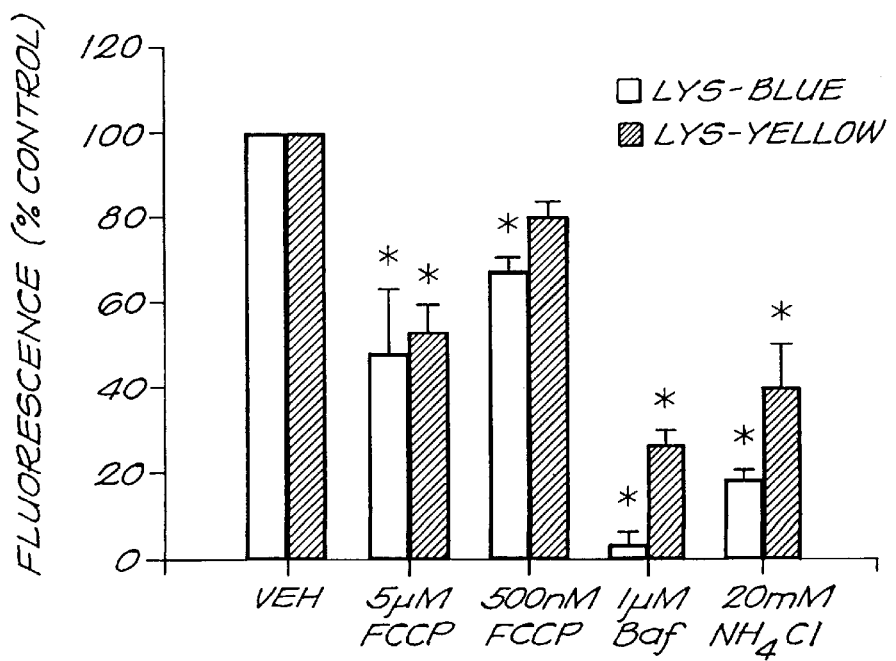

Through the use of a similar technique, putative lysosomal function was assessed by the quantitation of Lysosensor™ Yellow/Blue DND-160 uptake. In an analogous way as with the transferrin conjugates, overall lysosomal number and pH can be quantitated with this probe which exhibits a predominantly blue fluorescent emission spectra in less acidic lysosomes and a yellow emission spectra which increases upon acidification. Although it is probable that proportion of this probe may also partition into other acidic compartments, it is thought that Lysosensor™ predominantly accumulates in lysosomes of somatic cells and its staining pattern has been reported to resemble that of markers for lysosomes (LAMP-1 and 2)(36). A slight drawback with this technique is the presence of a small amount of overlap between the excitation and emission spectra which are originating from the same parent molecule. However, as with the effects of baf A1 and NH$_4$Cl on endosomal function it was observed that both of these agents produced profound reductions in lysosomal functioning (FIG. 7B). Interestingly, FCCP also led to reductions in lysosomal function, albeit not as profound as those observed with baf A1 or NH$_4$Cl.

The abbreviations used hereinabove are: AD, Alzheimer's Disease; Aβ, amyloid β peptide; APP, amyloid precursor protein; APPsα, α-secretase cleaved N-terminal ectodomain of APP; baf A1, bafilomycin A1; C100, C-terminal fragment containing the amyloid-β sequence; DG, 2-deoxy-D-glucose; DMEM, Dulbecco's modified Eagle's medium; FCCP, carbonyl cyanide p-(trifluoromethoxy) phenylhydrazone; NaA, sodium azide; PBS, phosphate-buffered saline; SDS-PAGE, sodium dodecyl sulfate-polyacrylamide gel electrophoresis.

It will be understood that the particular embodiments of the invention are shown by illustration and not as limitations of the invention. The principal features of the invention can be employed in various embodiments without departing from the scope of the present invention. All parts and percentages are by weight unless otherwise stated.

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A packaged pharmaceutical composition for treating a disease state associated with amyloidosis, comprising in a container a therapeutically effective amount of a mobile ionophore composition effective to prevent or decrease amyloidosis precursor protein (AAP) catabolism in APP-containing cells without substantially altering the viability of said APP-containing cells and a pharmaceutically acceptable vehicle, and instructions for using the composition.

2. The packaged pharmaceutical composition of claim 1 wherein said mobile ionophore composition is of the formula

wherein Y is a hydrophobic/lipophilic moiety; N is nitrogen; and Z is H, an alkyl group, an alkoxy group, or an electron-withdrawing moiety; provided that when Z is H, Y further comprises an electron-withdrawing moiety thereon.

3. The packaged pharmaceutical composition of claim 2 wherein Y is selected from the group consisting of aryl, aralkyl, aryl heterocycles, polycycyls, and heterocyclyls.

4. The packaged pharmaceutical composition of claim 2 wherein Y is selected from the group consisting of benzene, pyrrole, furan, thiophene, imidazole, oxazole thiazole, triazole, pyrazole, pyridine, pyrazine, pyridazine and pyrimidine, naphthyl, quinolyl, indolyl, tetralin, pyrrolidine, oxolane, thiolane, oxazole, piperidine, piperazine, morpholine, lactones, lactams, pyrrolidinones, lactones, sultams, and sultones.

5. The packaged pharmaceutical composition of claim 1 wherein said mobile ionophore composition is of the formula:

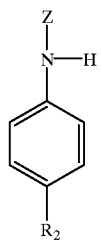

wherein R$_2$ is H, an alkyl group, an alkoxy group, or an electron-withdrawing moiety; Z is H, an alkyl group, an alkoxy group, or an electron-withdrawing moiety.

6. The packaged pharmaceutical composition of claim 5 wherein Z and R$_2$ are electron-withdrawing moieties.

7. The packaged pharmaceutical composition of claim 1 wherein said electron-withdrawing moieties are selected from the group consisting of trifluoromethanesulfonyl, trifluoromethoxy, trifluoroethoxy, and carbonyl cyano groups.

8. The packaged pharmaceutical composition of claim 5 wherein R$_2$ is an alkoxy group which contains one or more halogen atoms thereon.

9. The packaged pharmaceutical composition of claim 5 wherein R$_2$ is a mono-, di-, or tri-halomethoxy group.

10. The packaged pharmaceutical composition of claim 5 wherein R$_2$ is a trifluoromethoxy group and Z is —NC(CN)$_2$.

11. The packaged pharmaceutical composition of claim 5 wherein Z is —SO$_2$R$_4$ where R$_4$ is a mono-, di- or tri-halomethyl group.

12. The packaged pharmaceutical composition of claim 1 wherein said mobile ionophore composition is selected from the group consisting of carbonyl cyanide p-(trifluoromethoxy)phenylhydrazone, carbonyl cyanide m-chlorophenylhydrazone, N[4-(tetrafluoroethoxy)phenyl]-1,1,1-trifluoromethanesulfonamide, N-[4-chlorophenyl]-1, 1,1-trifluoromethanesulfonamide, N-[4-(tetrafluoromethoxy)phenyl]-1,1,1-trifluoromethanesulfonamide, N-[4-(methylthio)phenyl]-1, 1,1-trifluoromethanesulfonamide, N-[4-(t-butyl)phenyl]-1, 1,1-trifluoromethanesulfonamide, N-[4-fluorophenyl]1,1,1-trifluoromethanesulfonamide, N-phenyl-1,1,1-trifluoromethanesulfonamide, N-[4-(ethoxy)phenyl]-1,1,1-trifluoromethanesulfonamide, N-[4-(N,N-dimethylamino)phenyl]-1,1,1-trifluoromethanesulfonamide, N-[4-cyanophenyl]-1,1,1-trifluoromethanesulfonamide, and N-[4-(methylsulfonyl)phenyl]-1,1,1-trifluoromethanesulfonamide.

13. A packaged pharmaceutical composition for treating Alzheimer's disease, comprising in a container a therapeutically effective amount of a mobile ionophore composition effective to prevent or decrease amyloid precursor protein (AAP) catabolism in APP-containing cells without substantially altering the viability of said APP-containing cells and a pharmaceutically acceptable vehicle, and instructions for using the composition.

14. The packaged pharmaceutical composition of claim 13 wherein said mobile ionophore composition is of the formula

[Y—]—NH—[—Z]   (I)

wherein Y is a hydrophobic/lipophilic moiety; N is nitrogen; and Z is H, an alkyl group, an alkoxy group, or an electron-withdrawing moiety; provided that when Z is H, Y further comprises an electron-withdrawing moiety thereon.

15. The packaged pharmaceutical composition of claim 14 wherein Y is selected from the group consisting of aryl, aralkyl, aryl heterocycles, polycycyls, and heterocyclyls.

16. The packaged pharmaceutical composition of claim 14 wherein Y is selected from the group consisting of benzene, pyrrole, furan, thiophene, imidazole, oxazole, thiazole, triazole, pyrazole, pyridine, pyrazine, pyridazine and pyrimidine, naphthyl, quinolyl, indolyl, tetralin, pyrrolidine, oxolane, thiolane, oxazole, piperidine, piperazine, morpholine, lactones, lactams, pyrrolidinones, lactones, sultams, and sultones.

17. The packaged pharmaceutical composition of claim 13 wherein said mobile ionophore composition is of the formula:

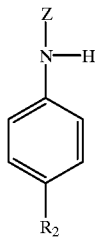
(II)

wherein $R_2$ is H an alkyl group, an alkoxy group, or an electron-withdrawing moiety; Z is H, an alkyl group, an alkoxy group, or an electron-withdrawing moiety.

18. The packaged pharmaceutical composition of claim 17 wherein Z and $R_2$ are electron-withdrawing moieties.

19. The packaged pharmaceutical composition of claim 13 wherein said electron-withdrawing moieties are selected from the group consisting of trifluoromethanesulfonyl, trifluoromethoxy, trifluoroethoxy, and carbonyl cyano groups.

20. The packaged pharmaceutical composition of claim 17 wherein $R_2$ is an alkoxy group which contains one or more halogen atoms thereon.

21. The packaged pharmaceutical composition of claim 17 wherein $R_2$ is a mono-, di-, or tri-halomethoxy group.

22. The packaged pharmaceutical composition of claim 17 wherein $R_2$ is a trifluoromethoxy group and Z is —NC$(CN)_2$.

23. The packaged pharmaceutical composition of claim 17 wherein Z is —$SO_2R_4$ where $R_4$ is a mono-, di- or tri-halomethyl group.

24. The packaged pharmaceutical composition of claim 13 wherein said mobile ionophore composition is selected from the group consisting of carbonyl cyanide p-(trifluoromethoxy)phenylhydrazone, carbonyl cyanide m-chlorophenylhydrazone, N[4-(tetrafluoroethoxy)phenyl]-1,1,1-trifluoromethanesulfonamide, N-[4-chlorophenyl]-1,1,1-trifluoromethanesulfonamide, N-[4-(tetrafluoromethoxy)phenyl]-1,1,1-trifluoromethanesulfonamide, N-[4-(methylthio)phenyl]-1,1,1-trifluoromethanesulfonamide, N-[4-(t-butyl)phenyl]-1,1,1-trifluoromethanesulfonamide, N-[4-fluorophenyl]-1,1,1-trifluoromethanesulfonamide, N-phenyl-1,1,1-trifluoromethanesulfonamide, N-[4-(ethoxy)phenyl]-1,1,1-trifluoromethanesulfonamide, N-[4-(N,N-dimethylamino)phenyl]-1,1,1-trifluoromethanesulfonamide, N-[4-cyanophenyl]-1,1,1-trifluoromethanesulfonamide, and N-[4-(methylsulfonyl)phenyl]-1,1,1-trifluoromethanesulfonamide.

* * * * *